(12) United States Patent
Hotter et al.

(10) Patent No.: US 8,513,224 B2
(45) Date of Patent: Aug. 20, 2013

(54) CRYSTALLINE FORM C OF TIGECYCLINE DIHYDROCHLORIDE AND METHODS FOR ITS PREPARATION

(75) Inventors: Andreas Hotter, Kundl (AT); Josef Wieser, Kundl (AT); Arthur Pichler, Kundl (AT); Martin Decristoforo, Kundl (AT)

(73) Assignee: Sandoz AG, Basel (CH)

( * ) Notice: Subject to any disclaimer, the term of this patent is extended or adjusted under 35 U.S.C. 154(b) by 186 days.

(21) Appl. No.: 13/133,164

(22) PCT Filed: Dec. 18, 2009

(86) PCT No.: PCT/EP2009/067513
§ 371 (c)(1),
(2), (4) Date: Aug. 15, 2011

(87) PCT Pub. No.: WO2010/070093
PCT Pub. Date: Jun. 24, 2010

(65) Prior Publication Data
US 2012/0022025 A1    Jan. 26, 2012

(30) Foreign Application Priority Data
Dec. 18, 2008   (EP) .................... 08172083

(51) Int. Cl.
| A01N 37/18 | (2006.01) |
| A61K 31/65 | (2006.01) |
| C07C 43/00 | (2006.01) |
| C07C 49/00 | (2006.01) |
| C07C 237/26 | (2006.01) |

(52) U.S. Cl.
USPC ........................................ 514/152; 552/205

(58) Field of Classification Search
USPC ........................ 552/205; 514/152
See application file for complete search history.

(56) References Cited

U.S. PATENT DOCUMENTS
| 5,675,030 A | 10/1997 | Krishnan et al. |
| 2008/0090789 A1 | 4/2008 | Tsiperman et al. |

FOREIGN PATENT DOCUMENTS
| WO | 2005056538 A1 | 6/2005 |
| WO | 2006128150 A2 | 11/2006 |
| WO | 2006130418 A1 | 12/2006 |
| WO | 2006130431 A1 | 12/2006 |
| WO | 2006130500 A2 | 12/2006 |
| WO | 2006130501 A2 | 12/2006 |
| WO | 2007127292 A2 | 11/2007 |
| WO | 2008066935 A2 | 6/2008 |
| WO | 2008155405 A1 | 12/2008 |

OTHER PUBLICATIONS

International Search Report and Written Opinion (mailed Feb. 9, 2010).
P.J. Petersen et al., Antimicrob. Agents Chemoth.1999; 43: 738-744.
R. Patel et al., Diagnostic Microbiology and Infectious Disease 2000; 38: 177-179.
H.W. Boucher et al., Antimicrob. Agents Chemoth. 44: 2225-2229 (2000).
D.J. Biedenbach et al., Diagnostic Microbiology and Infectious Disease 2001; 40: 173-177.
P.J. Petersen et al., Antimicrob. Agents Chemoth. 2002; 46: 2595-2601.
D. Milatovic et al., Antimicrob. Agents Chemoth. 47: 400-404 (2003).
T. Hirata et al., Antimicrob. Agents Chemoth. 2004; 48: 2179-2184.
G.A. Pankey, Journal of Antimicrobial Chemotherapy 2005; 56: 470-480.
R. Harris et al., P&T 2006; 31: 18-59.

*Primary Examiner* — Kendra D Carter
(74) *Attorney, Agent, or Firm* — Jeffrey S. Melcher; Manelli Selter PLLC

(57) ABSTRACT

The present invention relates to crystalline form C of Tigecycline dihydrochloride and to methods for the preparation of the same. Furthermore the present invention relates to the use of crystalline form C of Tigecycline dihydrochloride as an intermediate for the preparation of an anti-infective medicament. Moreover the present invention relates to pharmaceutical compositions comprising crystalline form C of Tigecycline dihydrochloride in an effective amount and to the use of crystalline form C of Tigecycline dihydrochloride as an anti-infective medicament.

14 Claims, 2 Drawing Sheets

CRYSTALLINE FORM C OF TIGECYCLINE DIHYDROCHLORIDE AND METHODS FOR ITS PREPARATION

CROSS-REFERENCE TO RELATED APPLICATIONS

This application is a national stage entry under 35 U.S.C. 371 of International Application No. PCT/EP2009/067513, filed 18 Dec. 2009, designating the United States. This application claims foreign priority under 35 U.S.C. 119 and 365 to European Patent Application No. 08172083.1, filed 18 Dec. 2008. The complete contents of these applications are incorporated herein by reference.

THE FIELD OF THE INVENTION

The present invention relates to crystalline form C of Tigecycline dihydrochloride and to methods for the preparation of the same. Furthermore the present invention relates to the use of crystalline form C of Tigecycline dihydrochloride as an intermediate for the preparation of an anti-infective medicament. Moreover the present invention relates to pharmaceutical compositions comprising crystalline form C of Tigecycline dihydrochloride in an effective amount and to the use of crystalline form C of Tigecycline dihydrochloride as an anti-infective medicament.

BACKGROUND OF THE INVENTION

Tigecycline, (4S,4aS,5aR,12aS)-4,7-Bis(dimethylamino)-9-[[[(1,1-dimethylethyl)amino]acetyl]amino]-1,4,4a,5,5a,6,11,12a-octahydro-3,10,12,12a-tetrahydroxy-1,11-dioxo-2-naphthacenecarboxamide, is a 9-t-butylglycylamido derivative of minocycline (Merck Index 14$^{th}$ Edition, monograph number 9432, CAS Registry Number 220620-09-7). Compared to other tetracycline antibiotics Tigecycline is more active against tetracycline-resistant strains and also more tolerable. Tigecycline possesses activity against bacterial isolates containing the two major determinants responsible for tetracycline-resistance: ribosomal protection and active efflux of the drug out of the bacterial cell. Furthermore Tigecycline possesses broad spectrum activity, e.g. it is active against gram-positive pathogens (e.g. methicillin-resistant *Staphylococcus aureus*, vancomycin-resistant Enterococci), gram-negative pathogens (e.g. *Acinetobacter baumannii*, *Stenotrophomonas maltophilia*) and anaerobic pathogens. At the moment Tigecycline is indicated for the treatment of complicated skin and soft-tissue infections and intra-abdominal infections. (P. J. Petersen et al., Antimicrob. Agents Chemoth. 1999; 43: 738-744. R. Patel et al., Diagnostic Microbiology and Infectious Disease 2000; 38: 177-179. H. W. Boucher et al., Antimicrob. Agents Chemoth. 44: 2225-2229. D. J. Biedenbach et al., Diagnostic Microbiology and Infectious Disease 2001; 40: 173-177. P. J. Petersen et al., Antimicrob. Agents Chemoth. 2002; 46: 2595-2601. D. Milatovic et al., Antimicrob. Agents Chemoth. 47: 400-404. T. Hirata et al., Antimicrob. Agents Chemoth. 2004; 48: 2179-2184. G. A. Pankey, Journal of Antimicrobial Chemotherapy 2005; 56: 470-480. R. Harris et al., P&T 2006; 31: 18-59.).

U.S. Pat. No. 5,675,030 claims a method of extracting Tigecycline dihydrochloride of unknown solid state.

WO 2005/056538, WO 2006/130418, WO 2006/130431, WO 2006/130500 and WO 2006/130501 disclose Tigecycline, acid addition salts of Tigecycline and processes of preparing the same as well. However, in literature no crystalline Tigecycline dihydrochloride or a method for its preparation is described.

Tigecycline is available on the market as lyophilized powder for injection, the originator is Wyeth. During the formulation process Tigecycline is first dissolved in water and then lyophilized. Therefore a crystalline form of Tigecycline or an alternative crystalline acid addition salt of Tigecycline should show high water solubility. The inventors of the present invention surprisingly found that crystalline form C of Tigecycline dihydrochloride clearly shows the highest water solubility compared with any of the crystalline forms of Tigecycline or Tigecycline hydrochloride.

Generally, crystalline solids have improved chemical and physical stability over the amorphous form and forms with low crystallinity, therefore crystalline Tigecycline dihydrochloride is more preferred than amorphous Tigecycline dihydrochloride. Thus there remains a need for crystalline Tigecycline dihydrochloride with high water solubility and suitable stability properties for the formulation of an anti-infective medicament.

SUMMARY OF THE INVENTION

In one embodiment, the present invention refers to crystalline form C of Tigecycline dihydrochloride.

Crystalline form C of Tigecycline dihydrochloride can be described by an X-ray powder diffraction pattern comprising peaks at 2-theta angles of 4.7°±0.2°, 7.6±0.2°, 9.4±0.2°, 10.4±0.2°, 12.7±0.2°, 14.4±0.2°, 15.3±0.2°, 20.7±0.2°, 21.5±0.2°, 23.2±0.2°, 25.6±0.2° and 26.4±0.2°.

Alternatively crystalline form C of Tigecycline dihydrochloride can be described by an infrared spectrum comprising peaks at wavenumbers of 3274±2 cm$^{-1}$, 2400±2 cm$^{-1}$, 1671±2 cm$^{-1}$, 1585±2 cm$^{-1}$, 1540±2 cm$^{-1}$, 1489±2 cm$^{-1}$, 1434±2 cm$^{-1}$, 1361±2 cm$^{-1}$, 1289±2 cm$^{-1}$, 1241±2 cm$^{-1}$, 1199±2 cm$^{-1}$, 1106±2 cm$^{-1}$, 1056±2 cm$^{-1}$, 1027±2 cm$^{-1}$, 1002±2 cm$^{-1}$, 936±2 cm$^{-1}$, 879±2 cm$^{-1}$, 806±2 cm$^{-1}$, 783±2 cm$^{-1}$ and 716±2 cm$^{-1}$.

A process for the preparation of crystalline form C of Tigecycline dihydrochloride comprising the steps of:
a) slurrying Tigecycline in acetonitrile or a mixture of acetonitrile with methylene chloride;
b) adding 2.0 to 2.2 equivalents hydrochloric acid to the suspension;
c) stirring the suspension at a temperature ranging from room temperature to the boiling point of the used solvent or solvent mixture;
d) isolating crystalline form C of Tigecycline dihydrochloride is also subject matter of the present invention.

Furthermore the present invention relates to the use of crystalline form C of Tigecycline dihydrochloride as an intermediate for preparing an anti-infective medicament.

Moreover the present invention relates to pharmaceutical compositions comprising crystalline form C of Tigecycline dihydrochloride in an effective amount.

In addition the present invention refers to the use of crystalline form C of Tigecycline dihydrochloride as an anti-infective medicament.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and from reading the other parts of the present disclosure.

DETAILED DESCRIPTION OF THE INVENTION

As used herein the term "amorphous" relates to solid material which lacks a regular crystalline structure.

The term "room temperature" as used herein indicates that the applied temperature is not critical and that no exact temperature value has to be kept. Usually, "room temperature" is understood to mean temperatures of about 15° C. to about 25° C. [see e.g. EU Pharmacopoeia 6.0, 1.2 (2008)].

The term "concentrated hydrochloric acid" relates to hydrochloric acid having a hydrochloride concentration of 37%.

The present invention relates to crystalline form C of Tigecycline dihydrochloride. The chemical structure of Tigecycline dihydrochloride is shown in Figure A.

Figure A: Chemical structure of Tigecycline dihydrochloride

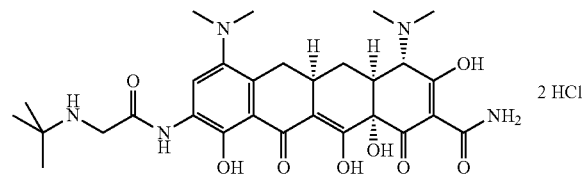

The crystalline form C of Tigecycline dihydrochloride may be characterized e.g. by a typical X-ray powder diffraction pattern or an infrared spectrum. Each of these characteristics on its own is sufficient to unambiguously define and identify the crystalline form of Tigecycline dihydrochloride but they also may be combined with each other.

The present invention relates to crystalline form C of Tigecycline dihydrochloride characterized by an X-ray powder diffraction pattern with peaks at 2-theta angles of 4.7°±0.2°, 7.6±0.2°, 9.4±0.2°, 10.4±0.2°, 12.7±0.2°, 14.4±0.2°, 15.3±0.2°, 20.7±0.2°, 21.5±0.2°, 23.2±0.2°, 25.6±0.2° and 26.4±0.2°.

Figure 1:
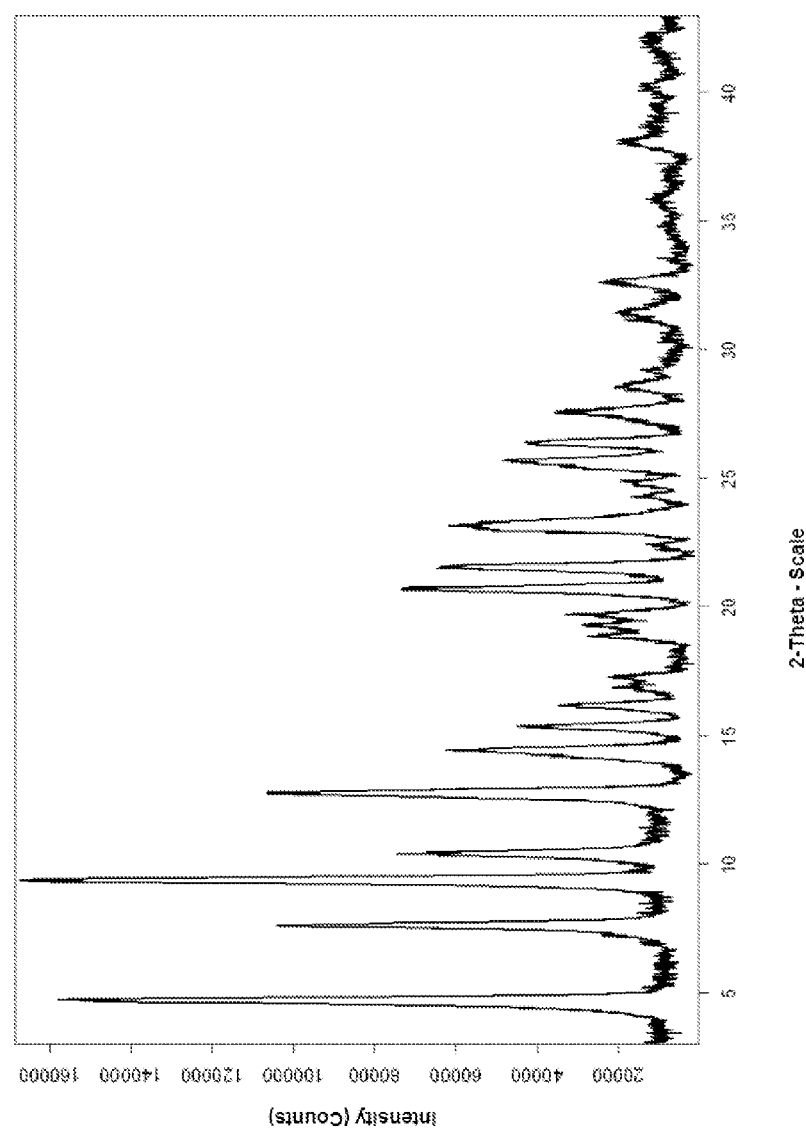
FIG. 1: X-ray powder diffraction pattern of crystalline form C of Tigecycline dihydrochloride

A characteristic X-ray powder diffraction pattern of crystalline form C of Tigecycline dihydrochloride is shown in FIG. 1 and some characteristic peaks are listed in Table 1.

Accordingly, in a preferred embodiment, the present invention relates to crystalline form C of Tigecycline dihydrochloride characterized by an X-ray powder diffraction pattern substantially in accordance with Table 1 and FIG. 1.

TABLE 1

Characteristic X-Ray Powder Diffraction (XRPD) peaks of crystalline form C of Tigecycline dihydrochloride

| Angle [°2-Theta] | Relative Intensity [%] |
| --- | --- |
| 4.7 | 94 |
| 7.6 | 63 |

TABLE 1-continued

Characteristic X-Ray Powder Diffraction (XRPD) peaks of crystalline form C of Tigecycline dihydrochloride

| Angle [°2-Theta] | Relative Intensity [%] |
| --- | --- |
| 9.4 | 100 |
| 10.4 | 45 |
| 12.7 | 64 |
| 14.4 | 37 |
| 15.3 | 27 |
| 20.7 | 45 |
| 21.5 | 39 |
| 23.2 | 37 |
| 25.6 | 29 |
| 26.4 | 26 |

Figure 2:
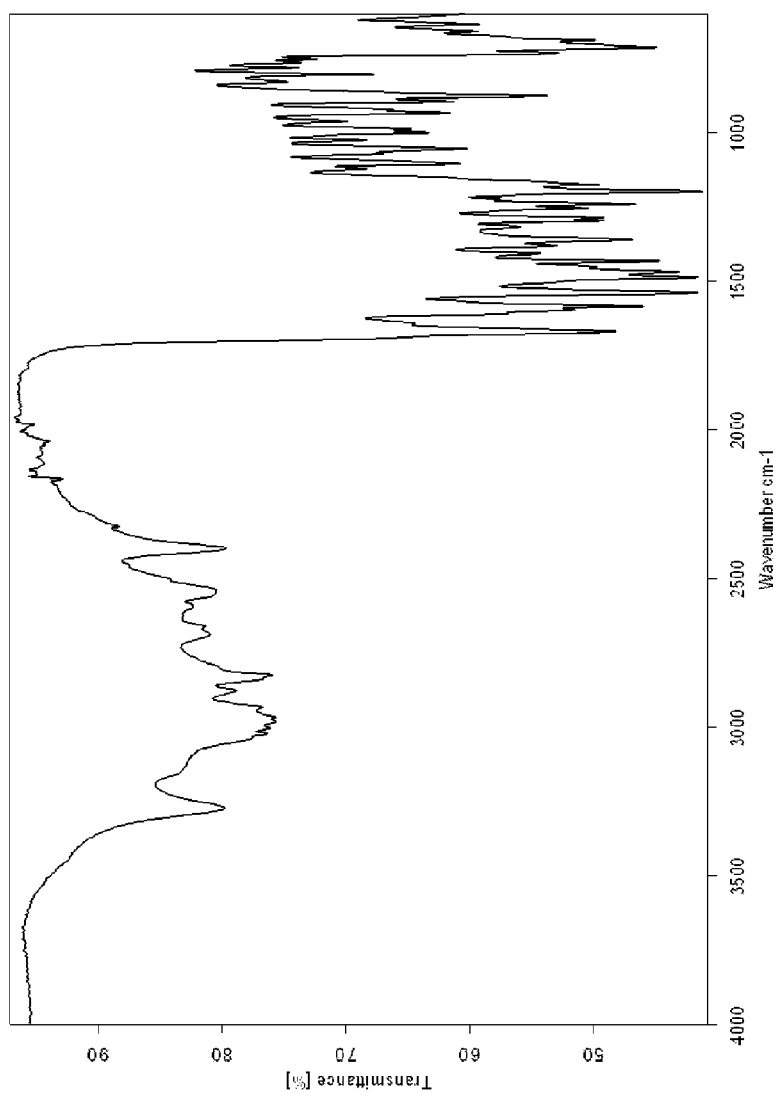
FIG. 2: Infrared spectrum of crystalline form C of Tigecycline dihydrochloride

Crystalline form C of Tigecycline dihydrochloride also may be characterized by a typical infrared spectrum as shown in FIG. 2. Accordingly in a further preferred embodiment, the present invention relates to crystalline form C of Tigecycline dihydrochloride characterized by an infrared spectrum substantially in accordance with FIG. 2. Characteristic bands are present at wavenumbers of $3274\pm2$ $cm^{-1}$, $2400\pm2$ $cm^{-1}$, $1671\pm2$ $cm^{-1}$, $1585\pm2$ $cm^{-1}$, $1540\pm2$ $cm^{-1}$, $1489\pm2$ $cm^{-1}$, $1434\pm2$ $cm^{-1}$, $1361\pm2$ $cm^{-1}$, $1289\pm2$ $cm^{-1}$, $1241\pm2$ $cm^{-1}$, $1199\pm2$ $cm^{-1}$, $1106\pm2$ $cm^{-1}$, $1056\pm2$ $cm^{-1}$, $1027\pm2$ $cm^{-1}$, $1002\pm2$ $cm^{-1}$, $936\pm2$ $cm^{-1}$, $879\pm2$ $cm^{-1}$, $806\pm2$ $cm^{-1}$, $783\pm2$ $cm^{-1}$ and $716\pm2$ $cm^{-1}$.

In one embodiment, the present invention provides a process for the preparation of crystalline form C of Tigecycline dihydrochloride, comprising the steps of:
a) slurrying Tigecycline in acetonitrile or a mixture of acetonitrile with methylene chloride;
b) adding 2.0 to 2.2 equivalents hydrochloric acid to the suspension;
c) stirring the suspension at a temperature ranging from room temperature to the boiling point of the used solvent or solvent mixture;
d) isolating crystalline form C of Tigecycline dihydrochloride Any form of Tigecycline may be used in step a) of the above process, e.g. amorphous forms, crystalline forms, mixtures of amorphous and crystalline forms, mixtures of different crystalline forms, hydrates or solvates. Suitable crystalline forms may be forms I to V of WO 2006/128150, forms I and II of WO 2007/127292, any of the forms disclosed in WO 2008/066935 or mixtures thereof.

Tigecycline preferably is used at a concentration ranging from 5 to 100 g/L, more preferably from 5 to 50 g/L and most preferably from 5 to 20 g/L.

It was found that crystalline form C of Tigecycline dihydrochloride does crystallize by using solvents like acetonitrile or mixtures of acetonitrile with methylene chloride. Mixtures of acetonitrile with methylene chloride are preferred, whereas the methylene chloride amount may range from 1% to 20%, preferably it ranges from 5% to 15%. Accordingly, the ratio of acetonitrile to methylene chloride ranges from 99:1 to 80:20 (v/v).

Any suitable hydrochloric acid can be used in step b) of the above described process. Either diluted or concentrated hydrochloric acid having a concentration in the range from 3 to 38% can be employed. Preferably hydrochloric acid having a concentration of about 10 to 37% most preferably having a concentration of about 18% is used.

The ratio of Tigecycline to hydrochloric acid employed may vary. When using less than 2.0 equivalents of hydrochloric acid a mixture of form C of Tigecycline dihydrochloride and form A of Tigecycline monohydrochloride is obtained. The inventors found that the less hydrochloric acid is used the more form A of Tigecycline monohydrochloride is obtained. On the other hand, an excess of hydrochloric acid may lead to material with a higher amorphous amount (see Table 2). Therefore, also crystalline form C of Tigecycline dihydrochloride containing e.g. less than 50% or less than 25% or less than 5% of amorphous material or crystalline form A of Tigecycline may be obtained. The inventors found out that the ideal ratio of Tigecycline to hydrochloric acid used is 2.0 to 2.2 equivalents hydrochloric acid to 1 equivalent Tigecycline (mol:mol) in order to obtain crystalline form C of Tigecycline dihydrochloride in essentially pure polymorphic form.

TABLE 2

Relation between HCl-amount and crystal form; ACNL:MED = 95:5 (v:v), c = 10 mg/mL, $T_{bath}$ = 83° C.;

| 5N HCl used [mol equivalents] | Form C [%] | Form A [%] | amorphous [%] |
|---|---|---|---|
| 1.4 | 33 | 67 | 0 |
| 1.6 | 55 | 45 | 0 |
| 1.8 | 90 | 10 | 0 |
| 2.0 | 100 | 0 | 0 |
| 2.5 | 40 | 0 | 60 |

The crystallization of form C of Tigecycline dihydrochloride would also take place at room temperature or even below. Nevertheless, in order to reach faster crystallization of Tigecycline dihydrochloride form C the suspension obtained in step c) is preferably stirred at elevated temperatures. Elevated temperature in this case means a temperature ranging from 30° C. to the boiling point of the used solvent or solvent mixture.

In step d) crystalline form C of Tigecycline dihydrochloride is isolated from the reaction mixture. Any conventional method such as filtration, centrifugation or evaporation of the solvent can be employed.

Form C of Tigecycline dihydrochloride is an anhydrous form, containing no water when stored at about 0% relative humidity and containing not more than about 0.8% to 1.7% e.g. when stored at about 50% relative humidity.

Tigecycline dihydrochloride form C crystallizes in thin elongated plates or fine needles having a length ranging from about 10-300 μm, depending on the crystallization velocity. Due to the greater particle size form C of Tigecycline dihydrochloride is better filterable than forms A and B of Tigecycline monohydrochloride. Therefore Tigecycline dihydrochloride form C is an especially suitable form for isolating Tigecycline dihydrochloride from synthesis by filtration especially in bulk production.

The finished dosage form contains lyophilized amorphous Tigecycline respectively Tigecycline hydrochloride. Before lyophilizing, Tigecycline respectively acid addition salts of Tigecycline are dissolved in water, thus water solubility is an important factor to consider. Table 3 shows the solubility data of the different crystalline forms of Tigecycline free base and crystalline forms A and B of Tigecycline hydrochloride compared with the one of crystalline form C of Tigecycline dihydrochloride.

As displayed in Table 3 crystalline form C of Tigecycline dihydrochloride clearly shows the highest water solubility and is therefore a particularly suitable form for the lyophilization process as an intermediate in order to prepare an anti-infective medicament.

TABLE 3

Water solubility of different crystalline forms of Tigecycline, Tigecycline hydrochloride and Tigecycline dihydrochloride form C

| Form | Concentration [mg/mL] | Base used [mg base equivalent] |
|---|---|---|
| WO 2006/128150 (free base) | | |
| I | 201 | 206 |
| II | 170 | 280 |
| III | 174 | 198 |
| IV | 322 | 387 |
| V | 134 | 180 |
| WO 2007/127292 (free base) | | |
| I | 54 | 156 |
| II | 76 | 198 |
| WO 2008/066935 (free base) | | |
| IX | 141 | 177 |
| XII | 174 | 180 |
| Present invention (acid addition salts) | | |
| A (xHCl) | 503 | 621 |
| B (xHCl) | 323 | 332 |
| C (x2HCl) | 562 | 696 |

Besides high water solubility crystalline form C of Tigecycline dihydrochloride of the present invention also shows good thermodynamical stability. Crystalline form C of Tigecycline dihydrochloride of the present invention represents a thermodynamically stable form, which means it does not convert into other crystalline or amorphous forms when storing it, even at elevated temperatures. For example crystalline form C of Tigecycline dihydrochloride did not change its crystal structure after storing for 7 days at 80° C.

Tigecycline must be available in a physically stable form as well, in order to avoid degradation and as a consequence the building of undesired byproducts. Table 4 compares the stability data of the different crystalline forms of Tigecycline free base and Tigecycline hydrochloride with these of crystalline form C of Tigecycline dihydrochloride from the present invention. After storing for 7 days at 80° C. one can see that forms I and II of WO 2006/128150 show a tremendous increase in total impurities. All the other crystalline forms of Tigecycline, Tigecycline hydrochloride and also Tigecycline dihydrochloride form C which have been tested showed satisfying stability data when considering that 80° C. for 7 days represent extreme conditions, which an active pharmaceutical ingredient never will experience in its life-cycle under ordinary circumstances.

In addition crystalline form C of Tigecycline dihydrochloride is more stable than the amorphous form. Table 4 displays that Tigecycline dihydrochloride form C with an amorphous amount of 20% is less stable than a pure polymorphic form C. Therefore crystalline form C of Tigecycline dihydrochloride in essentially pure polymorphic form is more preferred than amorphous Tigecycline dihydrochloride.

TABLE 4

Physical stability of crystalline forms of Tigecycline, Tigecycline hydrochloride and Tigecycline dihydrochloride form C at elevated temperatures

| Form | 4-Epi-Tigecycline at ambient conditions | 4-Epi-Tigecycline 7 days at 80° C. | Total impurities at ambient conditions | Total impurities 7 days at 80° C. |
|---|---|---|---|---|
| WO 2006/128150 (free base) | | | | |
| I | 0.36 | 2.15 | 0.75 | 11.20 |
| II | 1.04 | 10.83 | 1.60 | 18.44 |
| III | 0.16 | 2.18 | 0.16 | 4.46 |
| IV | 0.23 | 0.38 | 0.40 | 0.87 |
| V | <0.05 | 0.18 | 0.22 | 0.37 |
| WO 2007/127792 (free base) | | | | |
| I | 0.34 | 1.26 | 0.59 | 2.22 |
| II | 0.17 | 0.38 | 0.24 | 0.91 |
| WO 2008/066935 (free base) | | | | |
| IX | 0.15 | 0.70 | 0.43 | 2.13 |
| XII | 0.15 | 0.70 | 0.40 | 4.38 |
| Present invention (acid addition salts) | | | | |
| A (xHCl) | 0.84 | 0.89 | 1.07 | 1.81 |
| B (xHCl) | 0.93 | 1.60 | 1.91 | 4.19 |
| C (x2HCl) | 0.73 | 2.40 | 0.83 | 2.60 |
| C + 20% amorphous (x2HCl) | 1.73 | 4.34 | 1.81 | 4.88 |
| amorphous (x2HCl) | 4.97 | 16.42 | 5.05 | 18.82 |

On the whole crystalline form C of Tigecycline dihydrochloride possesses the highest water solubility and good physical and thermodynamical stability and is therefore a particularly useful form for the formulation of an anti-infective medicament.

Water solubility is an important factor to consider as Tigecycline respectively acid addition salts of Tigecycline are dissolved in water before lyophilizing during the formulation process. That's why crystalline form C of Tigecycline dihydrochloride of the present invention is a particularly suitable form to use for the formulation process.

In addition the thermodynamical and physical stability properties of crystalline form C of Tigecycline dihydrochloride of the present invention are suitable as well. Tigecycline dihydrochloride form C of the present invention neither showed a noticeable increase in impurities nor a conversion of the crystal structure after storing at extreme conditions.

Furthermore Tigecycline dihydrochloride form C is better filterable than forms A and B of Tigecycline hydrochloride and is therefore especially suitable for isolating Tigecycline dihydrochloride from synthesis by filtration, especially in bulk production.

Furthermore the present invention relates to the use of crystalline form C of Tigecycline dihydrochloride as an intermediate for preparing an anti-infective medicament.

Moreover the present invention relates to pharmaceutical compositions comprising crystalline form C of Tigecycline dihydrochloride in an effective amount.

In addition the present invention refers to the use of crystalline form C of Tigecycline dihydrochloride as an anti-infective medicament.

The invention is further described by reference to the following examples. These examples are provided for illustration purposes only and are not intended to be limiting the present invention in any way.

EXAMPLES

The X-ray powder diffraction pattern (XRPD) was collected on a Unisantis XMD 300 X-ray powder diffractometer with a position sensitive detector in parallel beam optics using the following acquisition conditions: tube anode: Cu, 40 kV, 0.8 mA; 3-43° theta/2theta; simultaneous detection of regions of 10° per step with detector resolution 1024, counting time 300 seconds per step. The sample was measured at room temperature in a standard sample holder on a rotating sample spinner. A typical precision of the 2-theta values is in the range of ± about 0.2° 2-theta. Thus a diffraction peak that appears at 5.0° 2-theta can appear between 4.8 and 5.2° 2-theta on most X-ray diffractometers under standard conditions.

The Infrared spectrum (IR) was collected on a MKII Golden Gate™ Single Reflection Diamond ATR (attenuated total reflection) cell with a Bruker Tensor 27 FTIR spectrometer with 4 $cm^{-1}$ resolution at ambient conditions. To collect a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 $cm^{-1}$. Thus, an infrared peak that appears at 1716 $cm^{-1}$ can appear between 1714 and 1718 $cm^{-1}$ on most infrared spectrometers under standard conditions.

Amounts of Tigecycline hydrochloride form A and amorphous Tigecycline dihydrochloride in Tigecycline dihydrochloride form C, presented in Table 2, were estimated by comparison of experimental infrared spectra from crystallization experiments with theoretical spectra calculated from normalized reference spectra of form C, form A and amorphous dihydrochloride. A comparison spectrum of Form C containing 30% form A was e.g. generated by calculating 0.7* (spectrum form $C$) + 0.3* (spectrum form $A$)

with the spectral calculator of Bruker's spectral software "OPUS". In this way theoretical spectra of form C containing between 10 and 90% Tigecycline monohydrochloride form A respectively amorphous Tigecycline dihydrochloride were calculated in 10% steps. Experimental spectra were then compared with these theoretical spectra, especially in the region from 3700-3300 $cm^{-1}$, to estimate the amount of Tigecycline hydrochloride form A and amorphous Tigecycline dihydrochloride in Tigecycline dihydrochloride form C.

Example 1

Preparation of Crystalline Form C of Tigecycline Dihydrochloride

A suspension was prepared by adding 190 mL of a acetonitrile/methylene chloride mixture (85:15; v:v) to 2038 mg Tigecycline. The suspension was stirred at room temperature for 30 minutes. Then 1.156 mL 5 N hydrochloric acid (2.1 equivalents) in 1 mL acetonitrile were slowly dropped to the suspension. The mixture was stirred at 70° C. for 20 hours, cooled down to room temperature and further stirred for 5 hours. The solid was filtered off and dried under vacuum at room temperature to obtain 2266 mg of crystalline form C of Tigecycline dihydrochloride (98.19% purity by HPLC; $H_2O$ KF: 1.7%).

Example 2

Preparation of Crystalline Form C of Tigecycline Dihydrochloride 40 mL XAD1600 were filled into a column (20 mm in diameter) and washed with 200 mL 4% aqueous sodium hydroxide, 250 mL demineralized water, 200 mL 0.1 M hydrochloric acid and again with 400 mL demineralized water. 17.3 g crude Tigecycline hydrochloride were dissolved in 200 mL water for injection and the obtained solution was pumped over the column with approximately 350 to 400 mL/h. 85 mL forerun were collected and thrown away before the pH decreased until 3-4. At said pH-value the eluate was collected. After the addition of the whole Tigecycline solution the column was finally washed with 400 mL 0.1 M hydrochloric acid.

The collected main pool was transferred into a 2 L Schmizo double coated reactor before, 488 mL methylene chloride were added. A pH of 8.0±0.1 was adjusted by the addition of 10 mL 20% aqueous sodium hydroxide while vigorously stirring. After stirring for 10 minutes the two phases were separated. The aqueous phase was washed two times with 488 mL methylene chloride, whereas the pH was held at 8.0±0.1 by the addition of either 0.1 M sodium hydroxide or 0.2 M hydrochloric acid. The obtained aqueous phase was thrown away. The collected methylene chloride phases were filtered over a fluted filter before the volume was reduced to 500 ml on the rotavapor (50-55° C., 500 mbar). Then 500 ml acetonitrile were added and the solution was again reduced to a volume of 230 ml. The solution is transferred into a 2 l Schmizo double coated reactor and 845 ml acetonitrile are added to obtain a total volume of 1075 ml. The solution was adjusted to a methylene chloride amount of 5% by the addition of approximately 20 ml methylene chloride. 0.2 g Tigecycline dihydrochloride (e.g. obtained from example 1) were added as seed crystals and Tigecycline crystallized at room temperature before 7.8 ml 5 M hydrochloric acid in 50 ml acetonitrile were added over a period of 15 to 20 minutes. The suspension was stirred for 16 hours at 20 to 25° C. whereas a change in color from yellow to orange was observed. To complete the crystallization the suspension was further stirred for 1 hour at 0 to 5° C. The solid was filtered off, washed with 80 ml of cold acetonitrile and dried under vacuum at room temperature for 16 hours to obtain 14 g of crystalline Tigecycline hydrochloride form C.

Example 3

Preparation of Crystalline Form C of Tigecycline Dihydrochloride 40 mL XAD1600 were filled into a column (20 mm in diameter) and washed with 200 mL 4% aqueous sodium hydroxide, 250 mL demineralized water, 200 mL 0.1 M hydrochloric acid and again with 400 mL demineralized water until pH≧5.0 was reached. 17.3 g crude Tigecycline hydrochloride were dissolved in 200 mL water for injection and the obtained solution was pumped over the column with approximately 350 to 400 mL/h. 85 mL forerun were collected and thrown away before the pH decreased until 3-4. At said pH-value the eluate was collected. After the addition of the whole Tigecycline solution the column was finally washed with 400 mL 0.1 M hydrochloric acid.

The collected main pool was transferred into a 2 L Schmizo double coated reactor before, 500 mL methylene chloride were added. A pH of 7.5±0.1 was adjusted by the addition of 10 mL 20% aqueous sodium hydroxide while vigorously stirring. After stirring for 10 minutes the two phases were separated. The aqueous phase was washed two times with 500 mL methylene chloride, whereas the pH was held at 7.5±0.1 by the addition of either 0.1 M sodium hydroxide or 0.2 M hydrochloric acid. The aqueous phase was thrown away and the combined methylene chloride phases were washed with 500 mL water. The methylene chloride phases were filtered over a fluted filter before 1400 mL acetonitrile were added under stirring. About 900 mL methylene chloride were removed on the rotavapor (50-55° C., 500-600 mbar) and at an inner temperature of about 40° C. 3.64 mL (2.0 mol equivalents) concentrated hydrochloric acid (37%) in 100 mL acetonitrile were added within 5-10 minutes under vigorous stirring. After the acid addition the volume was reduced to 1050-1060 mL on the rotavapor ($T_{bath}$=50-55° C., p=500-600 mbar) whereas the inner temperature was kept at 40° C. After the distillation the suspension was cooled to 20-25° C. within one hour and further stirred at this temperature for another hour. A change in color from yellow to orange was observed. The solid was filtered off, washed with 75 mL of cold acetonitrile and dried under vacuum at 35° C. for 16 hours to obtain 13-15 g of crystalline Tigecycline dihydrochloride form C.

Example 4

Water Solubility Testing

A UV-vis Lambda 35 spectrophotometer (Perkin-Elmer) was used (λ=347 nm, 1.0 cm quartz cells). Perkin Elmer® UV Win Lab-5.1 software was used.

A saturated solution of Tigecycline, Tigecycline hydrochloride or Tigecycline dihydrochloride in distilled water was prepared and the suspension was stirred at room temperature for 30 minutes with a stirring speed of 1000 U/min. The suspension was filtered through a 0.45 µm filter. Finally the resulting solution was diluted 10000-fold and measured against water at a wavelength of 347 nm.

| Form | Concentration [mg/ml] | Base used [mg base equivalent] |
|---|---|---|
| WO 2006/128150 (free base) | | |
| I | 201 | 206 |
| II | 170 | 280 |
| III | 174 | 198 |
| IV | 322 | 387 |
| V | 134 | 180 |
| WO 2007/127292 (free base) | | |
| I | 54 | 156 |
| II | 76 | 198 |
| WO 2008/066935 (free base) | | |
| IX | 141 | 177 |
| XII | 174 | 180 |

-continued

| Form | Concentration [mg/ml] | Base used [mg base equivalent] |
|---|---|---|
| Present invention (acid addition salts) | | |
| A (xHCl) | 503 | 621 |
| B (xHCl) | 323 | 332 |
| C (x2HCl) | 562 | 696 |

Example 5 shows the conditions of HPLC used in this application.

Example 5

HPLC

| HPLC apparatus | e.g. Agilent 1200 | | | | |
|---|---|---|---|---|---|
| Column | HALO C18, 2.7 μm, 100 × 4.6 mm (Advanced Material Technology Part. No. 92814-602) | | | | |
| System | gradient | | | | |
| Eluent A | buffer solution pH 6.7 | | | | |
| Eluent B | buffer solution pH 6.7/acetonitrile = 1/1 (v/v) | | | | |
| Flow rate | 1.5 mL/min | | | | |
| Oven temperature | 25° C. | | | | |
| Injection volume | 5 μL | | | | |
| Stop time | 12 min | | | | |
| Post time | 3 min | | | | |
| Detection | $\lambda$ = 250 nm | | | | |
| Gradient | t (min) | 0 | 5 | 10 | 11 | 12 |
| | % B | 25 | 35 | 100 | 100 | 25 |

The invention claimed is:

1. Crystalline Polymorphic form C of Tigecycline dihydrochloride having an X-ray powder diffraction pattern having peaks at 2-theta angles of 4.7°±0.2°, 7.6°±0.2°, 9.4°±0.2°, 10.4°±0.2°, 12.7°±0.2°, 14.4°±0.2°, 15.3°±0.2°, 20.7°±0.2°, 21.5°±0.2°, 23.2°±0.2°, 25.6°±0.2°, 26.4°±0.2°.

2. The crystalline polymorphic form C of Tigecycline dihydrochloride according to claim 1, having an X-ray powder diffraction pattern having a maximum peak at a 2-theta angle of 9.4°±0.2°.

3. Crystalline polymorphic form C of Tigecycline dihydrochloride, having an X-ray powder diffraction pattern in accordance with Table 1 and FIG. 1.

4. The crystalline polymorphic form C of Tigecycline dihydrochloride according to claim 1, having an infrared spectrum having peaks at wavenumbers of 3274±2 cm$^{-1}$, 2400±2 cm$^1$, 1671±2 cm$^{-1}$, 1585±2 cm$^{-1}$, 1540±2 cm$^{-1}$, 1489±2 cm$^{-1}$, 1434±2 cm$^{-1}$, 1361±2 cm$^{-1}$, 1289±2 cm$^{-1}$, 1241±2 cm$^{-1}$, 1199±2 cm$^{-1}$, 1106±2 cm$^{-1}$, 1056±2 cm$^{-1}$, 1027±2 cm$^{-1}$, 1002±2 cm$^{-1}$, 936±2 cm$^{-1}$, 879±2 cm$^{-1}$, 806±2 cm$^{-1}$, 783±2 cm$^{-1}$ and 716±2 cm$^{-1}$.

5. The crystalline polymorphic form C of Tigecycline dihydrochloride according to claim 3, having an infrared spectrum in accordance with FIG. 2.

6. The crystalline polymorphic form C of Tigecycline dihydrochloride according to claim 1, containing less than 50% amorphous material or crystalline form A of Tigecycline hydrochloride.

7. The crystalline polymorphic form C of Tigecycline dihydrochloride according to claim 1, containing less than 25% amorphous material or crystalline form A of Tigecycline hydrochloride.

8. The crystalline polymorphic form C of Tigecycline dihydrochloride according to claim 1, containing less than 5% amorphous material or crystalline form A of Tigecycline hydrochloride.

9. The crystalline polymorphic form C of Tigecycline dihydrochloride according to claim 1 is in an essentially pure polymorphic form C.

10. The crystalline polymorphic form C of Tigecycline dihydrochloride according to claim 1, wherein the Tigecycline dihydrochloride has a higher water solubility than forms A or B of Tigecycline hydrochloride.

11. A method for preparing crystalline polymorphic form C of Tigecycline dihydrochloride according to claim 1 comprising the steps of:
slurrying Tigecycline in acetonitrile or a mixture of acetonitrile with methylene chloride;
adding 2.0 to 2.2 equivalents hydrochloric acid to the suspension;
stirring the suspension at a temperature ranging from room temperature to the boiling point of the solvent or solvent mixture; and
isolating crystalline polymorphic form C of Tigecycline dihydrochloride.

12. The method according to claim 11, wherein the ratio of acetonitrile to methylene chloride ranges from 99:1 to 80:20 (v:v).

13. A pharmaceutical composition comprising an effective amount of crystalline polymorphic form C of Tigecycline dihydrochloride according to claim 1.

14. A method comprising using crystalline polymorphic form C of Tigecycline dihydrochloride according to claim 1 as an anti-bacterial medicament.

* * * * *